United States Patent [19]

Otten et al.

[11] Patent Number: 5,752,937
[45] Date of Patent: May 19, 1998

[54] REINFORCED SPLITTABLE MEDICAL INTRODUCER CANNULA

[75] Inventors: Lynn M. Otten, Blaine; Chris Christiansen, Oakdale, both of Minn.

[73] Assignee: Medtronic Inc., Minneapolis, Minn.

[21] Appl. No.: 846,636

[22] Filed: Apr. 30, 1997

[51] Int. Cl.[6] ................................................ A61M 5/178
[52] U.S. Cl. ............................ 604/161; 604/164; 604/282
[58] Field of Search ............................. 604/51–53, 158, 604/160, 161, 164, 280, 281, 282

[56] References Cited

U.S. PATENT DOCUMENTS

| | | |
|---|---|---|
| 4,166,469 | 9/1979 | Littleford . |
| 4,306,562 | 12/1981 | Osborne . |
| 4,377,165 | 3/1983 | Luther et al. . |
| 4,451,256 | 5/1984 | Weikl et al. ............................ 604/164 |
| 4,565,544 | 1/1986 | Muller et al. ........................... 604/164 |
| 4,596,559 | 6/1986 | Fleishhacker . |
| 4,921,479 | 5/1990 | Grayzel .................................. 604/164 |
| 4,983,168 | 1/1991 | Moorehead ............................. 604/161 |
| 5,180,372 | 1/1993 | Vegoe et al. . |
| 5,221,263 | 6/1993 | Sinko et al. ............................ 604/161 |
| 5,380,304 | 1/1995 | Parker .................................... 604/282 |
| 5,409,469 | 4/1995 | Schaerf .................................. 604/282 |
| 5,514,236 | 5/1996 | Avellanet et al. ...................... 604/282 |
| 5,639,276 | 6/1997 | Weinstock et al. ..................... 606/129 |

*Primary Examiner*—Sam Rimell
*Assistant Examiner*—Robert V. Racunas
*Attorney, Agent, or Firm*—Banner & Witcoff, Ltd.

[57] ABSTRACT

A reinforced splittable medical introducer cannula for insertion into a patient and delivering a catheter to a desired location within a patient comprising: (a) a body made of splittable material having sufficient strength for insertion through a needle puncture in the skin and through semi-hard tissue of a patient, the cylindrical body having a proximal end and a distal end, the cylindrical body defining a channel, the channel extending along the longitudinal length of the cylindrical body and between the proximal and distal ends of the cylindrical body, the channel further having a dimensions to permit the catheter to be inserted into the channel at the proximal end and through the cylindrical body and the distal end and delivered to the desired location within the patient; and (b) at least one strengthening strip co-extruded and embedded within the splittable material of the cylindrical body and extending at least partially along the longitudinal length of the cylindrical body, the material of the strengthening strip having a shear strength greater than the splittable material of the cylindrical body, whereby the strengthening strip can be pulled along the longitudinal length of the cylindrical body to cut and thereby split the medical introducer cannula so that the medical introducer cannula can be removed from the catheter while leaving the catheter in the desired location within the patient.

10 Claims, 1 Drawing Sheet

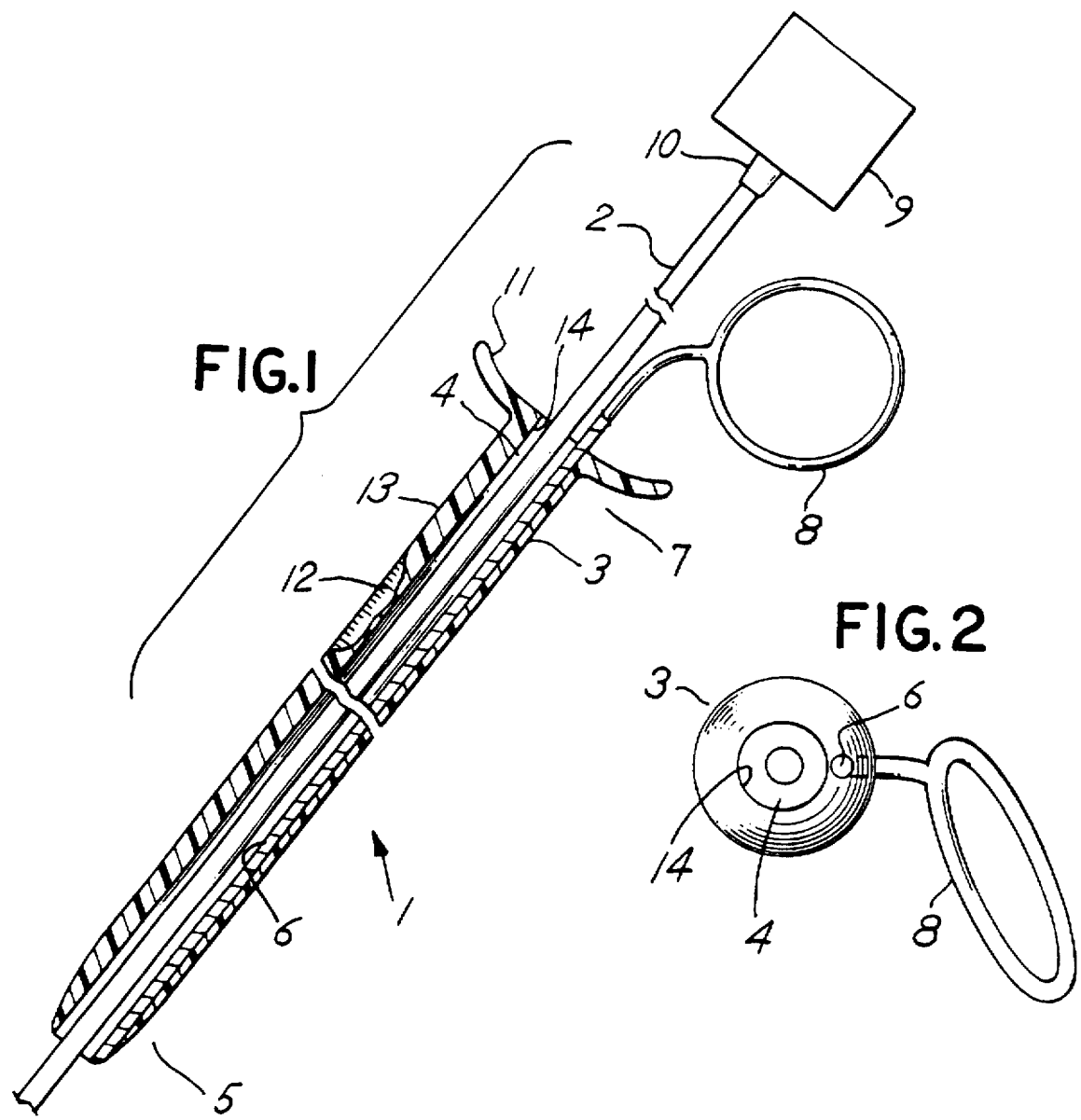

REINFORCED SPLITTABLE MEDICAL INTRODUCER CANNULA

BACKGROUND OF THE INVENTION

This invention relates to introducer cannulas by which medical devices, e.g. catheters and leads (hereinafter "catheters") for electrical stimulation generators, are inserted under the skin and introduced to the body, and especially to the spinal cord.

Introducer cannulas are employed to create openings through the skin for the insertion of numerous medical devices into soft tissue and organs, such as catheter leads for cardiac applications. For example, an introducer cannula can be inserted through a needle puncture and a catheter can then be passed through a central passageway of the introducer cannula and thus inserted through the skin and into a patient. The introducer cannula is then withdrawn from the patient, leaving the catheter in place in the patient. Generally, the catheter is attached to a medical apparatus before the introducer needle is removed. As a result, the introducer cannula presents removal problems that must be overcome without adversely effecting the insertion of the catheter into the patient or the attachment of the catheter to a medical device.

There are prior devices that are intended to overcome these problems. One is U.S. Pat. No. 4,377,165 which has an introducer that is splittable because it has a weakening along it that allows the introducer to be ripped apart when it is desired to remove the introducer. Similarly, U.S. Pat. No. 4,166,469 has an introducer sleeve that can be removed through a severing in the sleeve wall along the length thereof via a weakening, e.g. perforations, holes, through cuts, reduced wall thickness and integral cutting agents such as strings and the like.

Significant disadvantages arise in the use of these prior introducers because they have weakened structures to accomplish removal of the introducer. For example, because of these weakened structures, the introducer may split apart with little force and at the wrong time, e.g. when the introducer is first inserted into the patient, or before the catheter has been inserted completely through the introducer and into the patient, or before the catheter has been attached to the desired medical apparatus, or before the introducer has been removed from the patient and from the catheter. Such unplanned splitting of the introducer diminishes the effectiveness and usefulness of the introducer.

In addition, these prior introducers do not provide reliable separation, and tend to have sharp, ragged edges when they rip apart, giving rise to additional problems.

Moreover, these weakened structures, as well as prior structures that have integral cutting agents such as strings and the like are not strong enough to be effectively used for insertion into and through semi-hard tissue, such as ligaments and tendons, and therefore cannot be used for neurological applications. Thus, prior art introducers cannot be used effectively for the insertion of numerous medical devices, such as electrical signal generators and catheter leads for use as pain control in the spinal cord and brain. Because conventional introducers cannot be used for neurological applications, treatment of patients is severely limited and/or requires drastic surgery to deliver medical devices deep within patients to the treatment area.

Thus, it is an object of the present invention to provide an introducer cannula that does not have weakened structure to accomplish removal of the introducer cannula. It is a further object of the present invention to provide an introducer cannula that has greater strength than conventional introducers. It is a further objective of the present invention to provide an introducer cannula that can be used for insertion into and through semi-hard tissue and can be used for neurological applications. Another objective of the present invention is to provide a reinforced introducer cannula that can be easily removed from a patient and catheter as desired. A further objective of the present invention is to provide an introducer cannula that has structure for reliable, safe and efficient separation when desired, with minimal sharp, ragged edges. Another objective of the present invention is to provide an introducer cannula that can be more easily manufactured through co-extrusion, rather than manufacture of multiple component layers of integral cutting agents such as strings and the like.

SUMMARY OF THE INVENTION

A new medical introducer cannula has now been discovered that has no weakened structure for removal. This new medical introducer cannula has a strengthening strip or wire of material co-extruded and embedded into the material of the medical introducer cannula, and substantially along the longitudinal length of the introducer cannula. In the preferred embodiment, the strengthening strip runs along the entire longitudinal length of the introducer cannula. In the present invention, the material of the introducer cannula can be any suitable material, including those of prior introducers, such as plastic or fibrous material. The strengthening strip can be made of any suitable material that can act as a cutter, which can be pulled along the longitudinal length of the introducer cannula to cut and thereby split the introducer cannula for removal from the catheter without interfering with the insertion of the catheter into the patient or the attachment of the catheter to a medical device. Prior to being used as a cutter, the strengthening strip increases the strength of the introducer cannula, thereby preventing the introducer cannula from splitting at the wrong time. Examples of suitable material are suture materials or metal or metal alloys (including those containing titanium), and/or polymers, carbon/Kevlar® fibers.

In the present invention, the strengthening strip has a greater shear strength than the material of the introducer cannula. The cutting of the introducer cannula by the strengthening strip is accomplished by this difference in shear strength. In the preferred embodiment of the present invention, the strengthening strip is cylindrical, and has a gripping tab or finger pull structure at the proximal end of the introducer cannula that extends out of the introducer cannula, and which can be used by medical personnel to pull the strengthening strip so that it cuts and separates the introducer cannula along its longitudinal axis as desired. The result is the removal of the introducer cannula in a safe, reliable, and efficient manner.

The introducer cannula of the present invention can be inserted into the patient in all three ways used for prior introducers as described in U.S. Pat. No. 4,166,469. That is, the introducer cannula may be inserted through the needle or stylet that is used to puncture the skin of the patient, and remains in place when the needle is removed. Alternatively, the introducer cannula may be inserted by first inserting a guide wire through the needle, then removing the needle and then inserting the introducer cannula over the guide wire and into the patient, and then removing the guide wire, again leaving the introducer cannula in place. Third, and perhaps most commonly used today, the introducer cannula is located on the outer surface of the needle and is inserted into the patient upon inserting the needle into the patient. The needle is then removed, leaving the introducer cannula in place. The reinforced introducer cannula of the present invention has sufficient strength to withstand a great deal of pressure, and thus will not collapse when a needle is removed from it, and will not split or break apart when a medical device, such as a catheter is inserted, through the introducer cannula.

BRIEF DESCRIPTION OF THE DRAWING

The preferred embodiments of the invention(s) will hereafter be described with reference to the accompanying drawings. Each figure is briefly described as follows:

FIG. 1 is a perspective cut-away view of the reinforced splittable medical introducer cannula of the present invention.

FIG. 2 is a distal view of the reinforced splittable medical introducer cannula of the present invention.

DETAILED DESCRIPTION OF THE PREFERRED EMBODIMENTS

In FIG. 1, the reinforced splittable medical introducer cannula 1 of the present invention is illustrated, along with a catheter 2. As shown in FIGS. 1 and 2, medical introducer cannula 1 comprises a cylindrical body 3 defining a central passageway 4. Catheter 2 can be inserted through central passageway 4 as desired. Preferably, cylindrical body 3 is made of plastic or fibrous material, including materials used for prior introducers, e.g. Hytrel® or Tecoflex®. As shown in FIG. 2, cylindrical body 3 can have a filament structure having sufficient strength to prevent collapse of the inner wall 14 of cylindrical body 3 when a puncture needle is withdrawn from the patient via central passageway 4, and to prevent splitting of cylindrical body 3 when a medical device is inserted into and through central passageway 4 and into a patient. If desired, the distal end 5 of introducer cannula 1 can be tapered as shown in FIG. 1 to aid in its insertion into a patient. Introducer cannula 1 also has strengthening strip 6 co-extruded with the material of cylindrical body 3 and embedded within cylindrical body 3. In the preferred embodiment, strengthening strip runs along the longitudinal length of cylindrical body 3, and most preferably along its entire length.

In the preferred embodiment, at the proximal end 7 of introducer cannula 1, the strengthening strip extends out of the introducer cannula 1, and has a finger pull 8. Finger pull 8 can be gripped and pulled as desired by medical personnel, thereby permitting strengthening strip 6 to cut along cylindrical body 3, and splitting introducer cannula 1 so that it can be removed from catheter 2 as desired.

The strengthening strip can be made of any suitable material that can act as a cutter, which can be pulled along the longitudinal length of cylindrical body 3 of introducer cannula 1, thereby splitting introducer cannula 1 for removal from catheter 2 without interfering with the insertion of catheter 2 into the patient or the attachment of catheter 2 to a medical device 9 through connector 10. Prior to being used as a cutter, the strengthening strip 6 increases the strength of introducer cannula 1, thereby preventing introducer cannula 1 from splitting at the wrong time. Examples of suitable material are suture materials or metal or metal alloys, including those containing titanium, and/or polymers, carbon/Kevlar® fibers.

In the present invention, strengthening strip 6 has a greater shear strength than the material of cylindrical body 3 of introducer cannula 1. The cutting of the introducer cannula 1 by the strengthening strip 6 is accomplished by this difference in shear strength. In the preferred embodiment of the present invention, strengthening strip 6 is cylindrical.

In the preferred embodiment, introducer cannula 1 may have a wing or finger pad 11 at proximal end 7 to permit medical personnel to better grip introducer cannula 1 and exert greater force to insert introducer cannula 1 deep into the patient as desired. Further, introducer cannula 1 may have markings 12, such as centimeter markings, on its outside wall 13, so that medical personnel can see how deep the introducer cannula has been inserted into the patient.

Those skilled in that art will recognize that the preferred embodiments may be altered or amended without departing from the true spirit and scope of the invention, as defined in the accompanying claims. Thus, while various alterations and permutations of the invention are possible, the invention is to be limited only by the following claims and equivalents.

What is claimed is:

1. A reinforced splittable medical introducer cannula for insertion into a patient and delivering a catheter to a desired location within a patient comprising:
    (a) a body made of splittable material having sufficient strength for insertion through a needle puncture in the skin and through semi-hard tissue of a patient, the body having a proximal end and a distal end, the body defining a channel, the channel extending along the longitudinal length of the body and between the proximal and distal ends of the body, the channel further having a dimension to permit the catheter to be inserted into the channel at the proximal end and through the body and the distal end and delivered to the desired location within the patient; and
    (b) at least one strengthening strip embedded within the splittable material of the body and extending at least partially along the longitudinal length of the body, the material of the strengthening strip having a shear strength greater than the splittable material of the body, whereby the strengthening strip can be pulled along the longitudinal length of the body and is capable of cutting the body to thereby split the introducer cannula so that the introducer cannula can be removed from the catheter while leaving the catheter in the desired location within the patient.

2. The reinforced splittable medical introducer cannula of claim 1 wherein the body is cylindrical.

3. The reinforced splittable medical introducer cannula of claim 1 wherein the strengthening strip is co-extruded with the splittable material of the body.

4. The reinforced splittable medical introducer cannula of claim 1 wherein the strengthening strip further has an end portion that is not embedded in the material of the body of the reinforced splittable introducer cannula, said end portion capable of being gripped and pulled along the longitudinal length of the body.

5. The reinforced splittable medical introducer cannula of claim 2 wherein the end portion of the strengthening strip is located at the proximal end of the body of the reinforced splittable introducer cannula.

6. The reinforced splittable medical introducer cannula of claim 1 wherein the distal end of the body of the reinforced splittable introducer cannula is tapered.

7. The reinforced splittable medical introducer cannula of claim 1 wherein the strengthening strip is cylindrical.

8. The reinforced splittable medical introducer cannula of claim 1 wherein the strengthening strip extends along the entire longitudinal length of the reinforced splittable introducer cannula.

9. The reinforced splittable medical introducer cannula of claim 1 wherein the proximal end of the body further has a wing so that greater force can be exerted at the proximal end to insert the reinforced splittable introducer cannula more deeply into the patient as desired.

10. The reinforced splittable medical introducer cannula of claim 1 wherein the body has an outside wall having markings so that medical personnel can see how far the reinforced splittable introducer cannula has been inserted into a patient.

* * * * *